United States Patent [19]

Giacobbe et al.

[11] Patent Number: 4,503,245

[45] Date of Patent: * Mar. 5, 1985

[54] SOLVENT AND CATALYST RECOVERY AND RECYCLE IN THE MANUFACTURE OF PHENOXYBENZOIC ACID DERIVATIVES

[75] Inventors: Thomas J. Giacobbe, Skillman; Thomas N. Williams, Jr., Plainfield, both of N.J.; James M. Horn, Richmond, Va.

[73] Assignee: Rhone-Poulenc, Inc., Monmouth Junction, N.J.

[*] Notice: The portion of the term of this patent subsequent to Jun. 26, 2001 has been disclaimed.

[21] Appl. No.: 548,364

[22] Filed: Nov. 3, 1983

Related U.S. Application Data

[63] Continuation of Ser. No. 518,975, Aug. 2, 1983, Pat. No. 4,456,767, which is a continuation of Ser. No. 286,942, Jul. 27, 1981, abandoned.

[51] Int. Cl.$^3$ ............................................. C07C 51/16
[52] U.S. Cl. ..................................... 562/414; 562/416
[58] Field of Search ................................ 562/414, 416

[56] References Cited

U.S. PATENT DOCUMENTS

| | | | |
|---|---|---|---|
| 2,964,559 | 12/1960 | Burney et al. | 562/414 |
| 3,484,458 | 12/1969 | Stein et al. | 562/414 |
| 4,323,692 | 4/1982 | Tanger | 560/65 |

Primary Examiner—Alan Siegel
Attorney, Agent, or Firm—Scully, Scott, Murphy & Presser

[57] ABSTRACT

An improved process is provided for recovering and recycling reaction medium solvent and cobalt-containing cocatalyst in the oxidation of 3-(substituted phenoxy) toluene to provide the corresponding 3-(substituted phenoxy) benzoic acid, the latter being a useful intermediate in the manufacture of herbicides such as acifluorfen.

19 Claims, 3 Drawing Figures

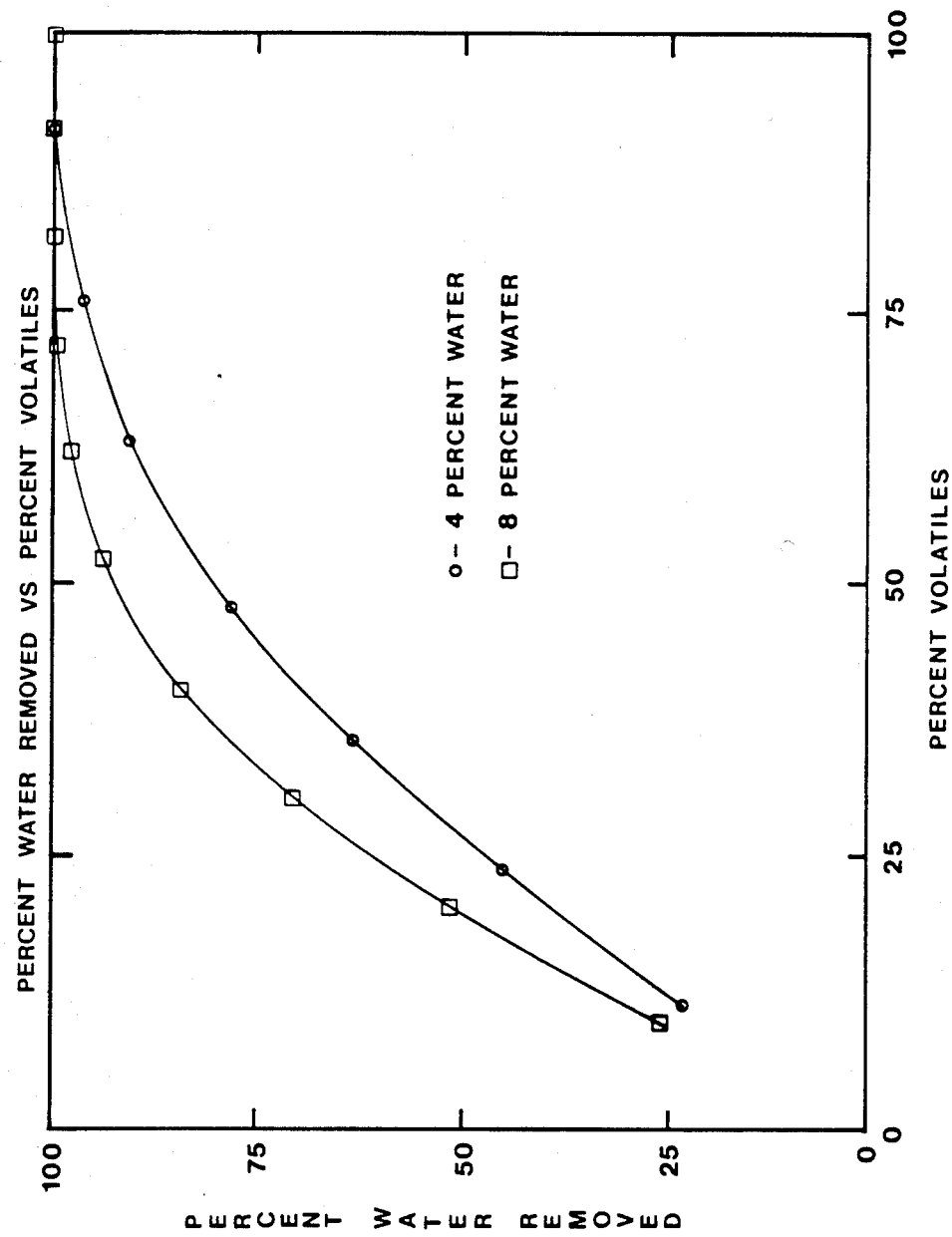

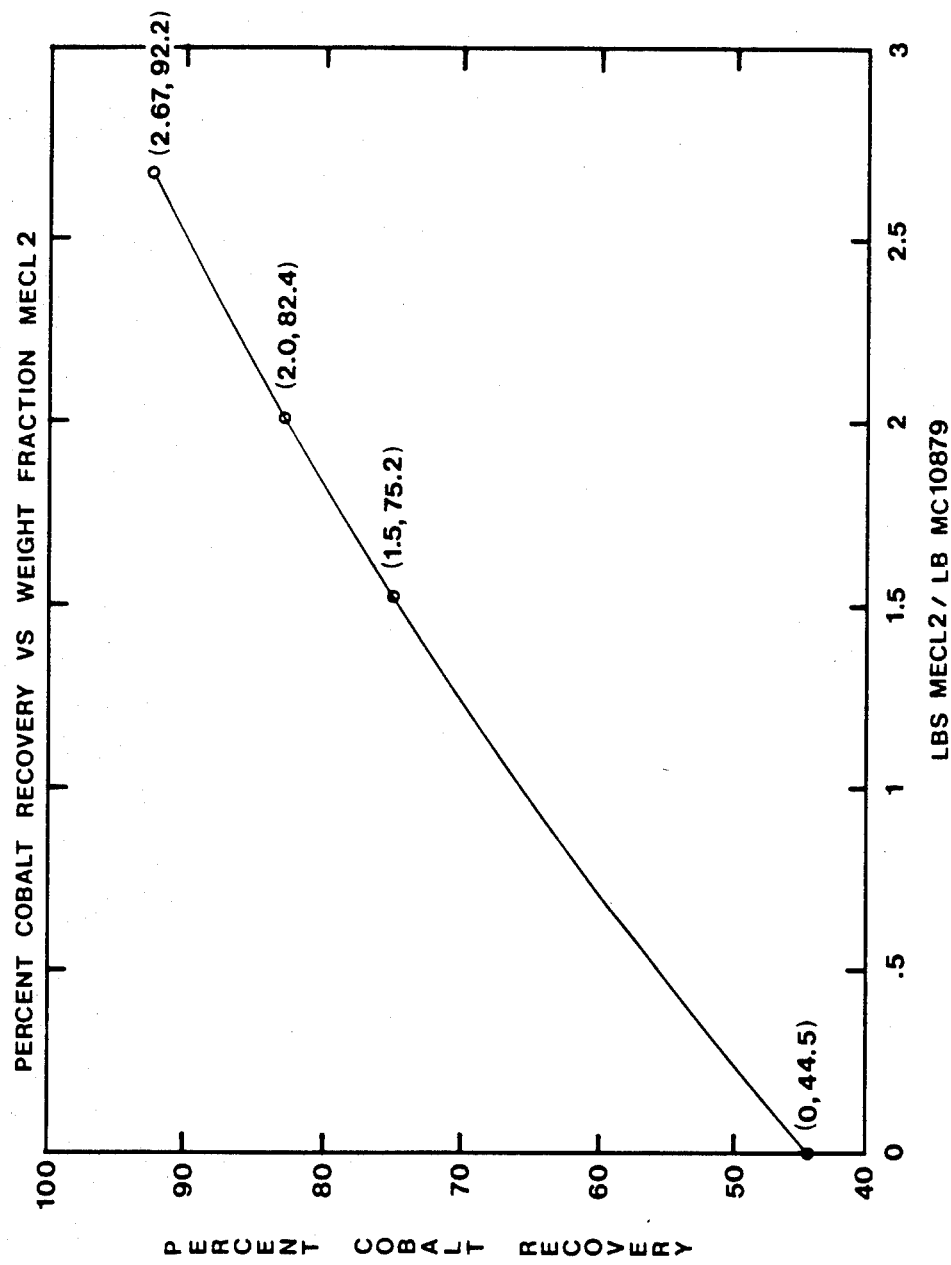

SOLVENT AND CATALYST RECOVERY AND RECYCLE IN THE MANUFACTURE OF PHENOXYBENZOIC ACID DERIVATIVES

This is a continuation of co-pending application Ser. No. 518,975 filed Aug. 2, 1983 now U.S. Pat. No. 4,456,767, which is a continuation of of U.S. Serial No. 286,942 filed July 27, 1982 now abandoned.

CROSS REFERENCE TO RELATED APPLICATIONS

This application discloses subject matter disclosed in commonly assigned, co-pending U.S. patent application Ser. No. 208,081 filed Nov. 18, 1980 as a continuation-in-part of U.S. patent application Ser. No. 067,508 filed Aug. 17, 1979, now abandoned, which in turn is a continuation-in-part of U.S. patent application Ser. No. 051,254, filed June 22, 1979, also abandoned. The disclosure of each of the aforesaid patent applications is incorporated by reference herein.

BACKGROUND OF THE INVENTION

This invention concerns a process for preparing phenoxybenzoic acid derivatives which are useful as herbicides, and in particular, acifluorfen, i.e., the compound 5-[2-chloro-4-(trifluoromethyl)phenoxy]-2-nitrobenzoic acid, which in the form of its sodium salt is commercially available as the product Tackle (Mobil Oil Corporation). Acifluorfen, which possesses the structure

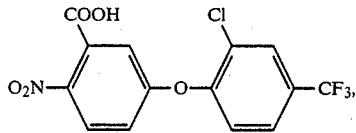

and related phenoxybenzoic acid derivatives constitute a class of highly effective herbicides for the post-emergence control of a variety of weeds such as certain broadleafs associated with soybeans.

Copending U.S. patent application Ser. No. 208,081 filed Nov. 18, 1980 and its predecessor applications Ser. Nos. 067,508, filed Aug. 17, 1979 and 051,254, filed June 22, 1979, both now abandoned) each describes a four-step synthesis of a class of phenoxybenzoic acid derivatives to which acifluorfen belongs. The sequence of steps comprising this synthesis is as follows:

STEP 1: Salt Formation

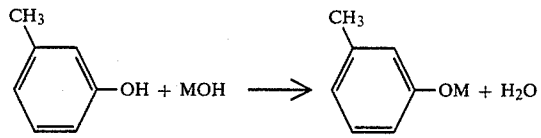

M is an alkali metal atom or ammonium ion.

STEP 2: Coupling

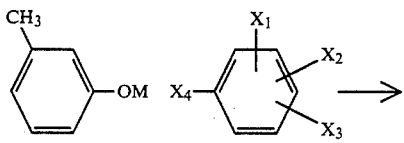

STEP 2: Coupling -continued

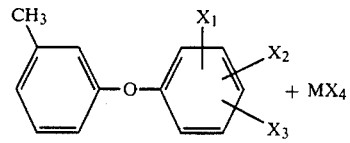

$X_1$, $X_2$ and $X_3$ each is H, F, Cl, Br, $CF_3$, $OCF_2CHZ_2$ (Z=Cl, F or Br), $OCF_3$, CN, $CO_2R$ (R=lower alkyl), $-C_6H_5$, O-alkyl, $NO_2$ or $SO_2$ (lower) alkyl and is F, Cl or Br, provided that at least one of $X_1$, $X_2$ and $X_3$ is other than H.

STEP 3: Oxidation

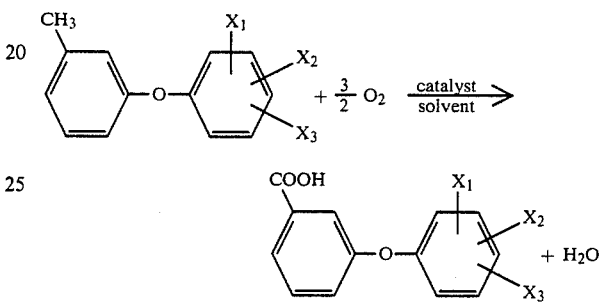

STEP 4: Nitration

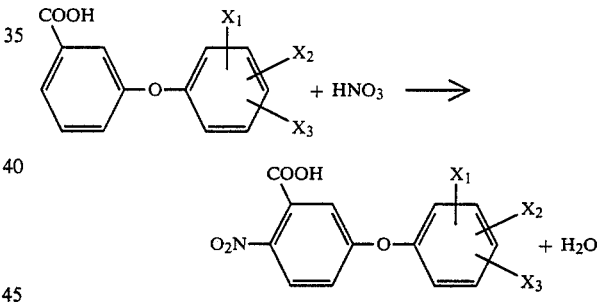

The carboxyl group in the product compounds can be made to undergo transformation to a variety of other groups, including salts, employing conventional procedures.

In oxidation step 3, the catalyst system comprises a source of cobalt compound and a source of bromide, compound, e.g., a combination of cobaltous acetate tetrahydrate and sodium bromide. The oxidation is carried out in a suitable inert solvent, e.g., any of the lower aliphatic carboxylic acids such as acetic acid, and in the presence of a free radical initiator, e.g., any of the peroxides such as hydrogen peroxide. Favorable process economics require an efficient system for catalyst and solvent recovery in this step. In accordance with the recycle procedures of the aforesaid U.S. patent applications, the cobalt compound and part of the bromide compound can be recovered and recycled by crystallizing the phenoxybenzoic acid derivative from the reaction solution, collecting the crystallized product on a basket centrifuge and recycling the mother liquors which contain the catalyst solvent and a few weight percent of phenoxybenzoic acid derivative to the oxidation step. The water of reaction can be removed from the recycled mother liquors by conventional means, e.g., fractional distillation or addition of acetic anhydride. The water is advantageously equal to or less than 1 weight percent in the recycled mother liquors and equal to or less than 2 weight percent after the addition of aqueous peroxide. The catalyst and acetic acid remaining on the phenoxybenzoic acid filter-cake can be recovered by dissolving the filter-cake in a suitable solvent such as methylene chloride and extracting this solution with water. The acetic acid, cobalt acetate, and sodium bromide partition into the aqueous phase which can then be added to the recycled mother liquors. Approximately 88 weight percent of the acetic acid and more than 95 weight percent of the cobalt and bromide are recovered in each recycle employing the foregoing procedures.

SUMMARY OF THE INVENTION

In accordance with the present invention, a process is provided for recovering and recycling solvent in the oxidation of a phenoxytoluene derivative to provide a phenoxybenzoic acid intermediate which is simpler than the solvent recovery and recycle procedures described in the U.S. patent applications referred to supra, and therefore represents an improvement over the latter.

Broadly defined, the invention herein is directed to a process for recovering and recycling solvent in the oxidation of a 3-(substituted phenoxy) toluene feed to the corresponding 3-(substituted phenoxy) benzoic acid employing a combination of a cobalt compound and a bromide compound as catalyst which comprises:

(a) distilling a first solvent from the oxidation reaction mixture containing 3-(substituted phenoxy) benzoic acid and cobalt compound;

(b) combining solvent-depleted reaction mixture from (a) with a second solvent which dissolves 3-(substituted phenoxy) benzoic acid and is capable of forming an immiscible layer with an aqueous solution of lower aliphatic carboxylic acid;

(c) combining solution of 3-(substituted phenoxy) benzoic acid from (b) with an aqueous solution of lower aliphatic carboxylic acid which dissolves the cobalt compound to extract cobalt compound from said solution;

(d) separating the solution layer of 3-(substituted phenoxy) benzoic acid from the aqueous solution layer of lower aliphatic carboxylic acid and dissolved cobalt compound;

(e) separating aqueous solution of lower aliphatic carboxylic acid from extracted cobalt compound resulting from step (c) and (d);

(f) recycling the first solvent recovered from (a) to serve as solvent in the oxidation of an additional quantity of 3-(substituted phenoxy) toluene feed.

In contrast to the five unit operations required by the solvent and catalyst recovery process of the aforestated U.S. patent applications, the process of this invention requires only three unit operations with a consequent significant savings in plant construction and operating costs.

BRIEF DESCRIPTION OF THE DRAWINGS

FIG. 2 is a graph showing the relationship between weight percent water removed and weight percent volatiles in the distillation step (a) of the invention; and, FIG. 3 is a graph showing the relationship between weight percent cobalt recovery and weight percent fraction of methylene chloride ($MeCl_2$) in step (c) of the invention.

DESCRIPTION OF THE PREFERRED EMBODIMENTS

Figure 1:
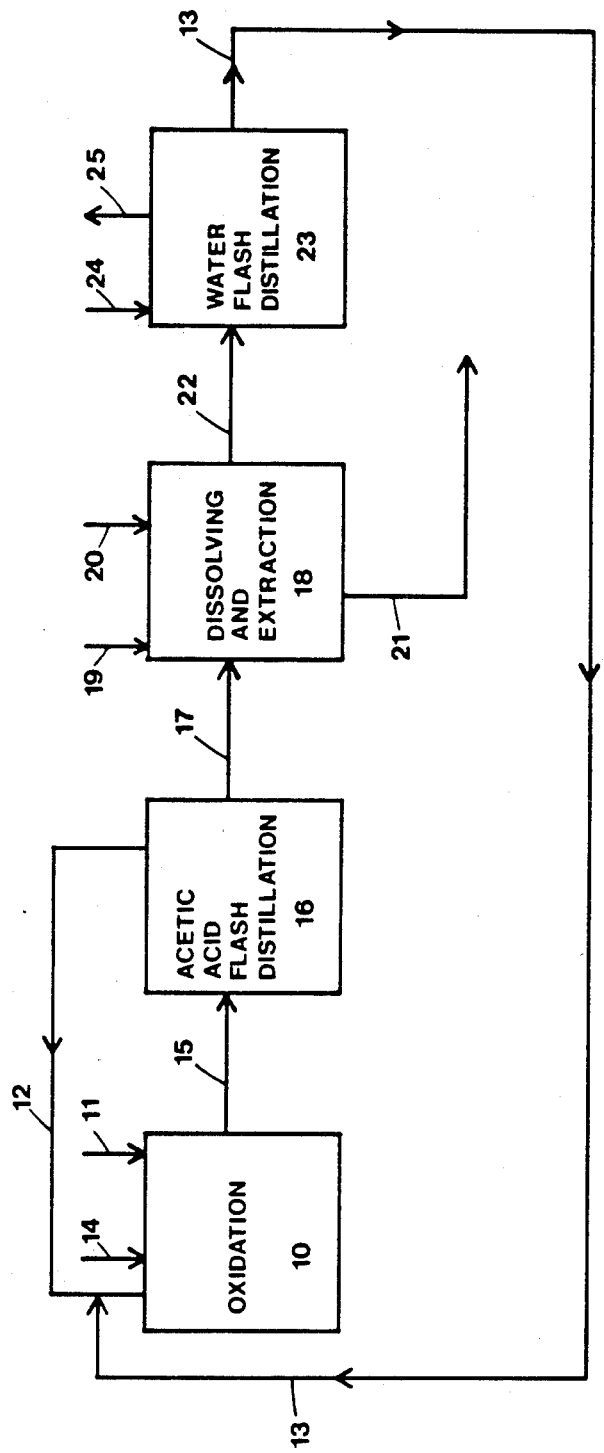
FIG. 1 is a flow diagram of one embodiment of the present invention.

In FIG. 1, a flow diagram illustrates one embodiment of the present invention as applied to the manufacture of a 3-(substituted phenoxy) benzoic acid intermediate i.e., 5-[2-chloro-4-(trifluoromethyl)phenoxy]-2-benzoic acid, which, when nitrated, provides the herbicide acifluorfen. The oxidation step which is carried out in unit 10 employs oxygen supplied through line 11 as air as the oxidizing agent, recycled acetic acid supplied through line 12 as the solvent, recycled cobaltous acetate tetrahydrate supplied through line 13 and sodium bromide supplied through line 14 as the cocatalysts and hydrogen peroxide as the free radical initiator. The oxidation mixture is transferred from oxidation unit 10 through line 15 to acetic acid flash distillation unit 16. The acetic acid is recovered and water is removed therefrom by taking two cuts in a flash distillation of the volatile components from the oxidation reaction. The first cut provides the means for removing water from the system, and this cut is sent to aqueous waste. The second cut from the flash distillation contains the remainder of the water and acetic acid and is made anhydrous by the addition of acetic anhydride with the glacial acetic acid being recycled to the next oxidation batch through line 12. The optimum point at which the first cut is made is based upon economic and material balance considerations. The data shown in FIG. 2 (generated on a laboratory scale) shows the percent water recovered vs the percent volatiles (water plus acetic acid) present in the oxidation solution. A typical oxidation solution contains about 4–8wt% water at the end of the reaction, and using FIG. 2, it is seen that about 30% of the volatiles must be flash distilled in order to remove about 60% of the water present. The acetic acid-depleted reaction product from unit 16 is transferred through line 17 to dissolving and extraction unit 18 where it is combined with a solvent for the product phenoxybenzoic acid intermediate such as methylene chloride supplied through line 19 (e.g., 2.67 lbs of methylene chloride per lb of crude phenoxybenzoic acid intermediate) and an aqueous lower aliphatic carboxylic acid such as acetic acid supplied through line 20 (e.g., 0.75 lb of 10% aqueous acetic acid per lb of crude phenoxybenzoic acid intermediate) to extract the cobaltous acetate tetrahydrate from the methylene chloride solution. The mixture of the dissolved intermediate, cobaltous acetate tetrahydrate and dilute acetic acid is agitated and heated to 60° C. under a slight pressure (18 psig). Extraction is effected at elevated temperature and slight pressure (e.g., 60° C., at 18 psig) to assure that all of the phenoxybenzoic acid intermediate remains in solution. Approximately 92–93% of the cobalt is recovered in the aqueous phase. The partitioning of the cobalt into the aqueous phase becomes less favorable as the amount of methylene choride is decreased (see FIG. 3). The methylene chloride layer (lower phase) is separated through line 21, mixed with acetic anhydride and stored for the subsequent nitration step to provide acifluorfen.

The upper aqueous acetic acid solution of cobaltous acetate tetrahydrate is passed through line 22 with the acetic acid being separated from the cobalt compound in flash evaporation unit 23 at atmospheric pressure with 3-(substituted phenoxy)toluene feed supplied through line 24 acting as a heat transfer medium and steam being released through line 25. No decomposition of the aforesaid phenoxytoluene intermediate was observed during the flash distillation and the cobalt compound appeared to be dissolved in this fluid. A negligible amount of the phenoxy toluene intermediate was lost by steam-distillation to the aqueous condensate. Cobaltous acetate tetrahydrate recovered from flash evaporation unit 23 is recycled to oxidation unit through line 13.

Approximately 95% of the bromide cocatalyst was lost during the oxidation and the acetic acid flash distillations and had to be replenished before effecting oxidation of a further quantity of starting compound. Thus, after completing the flash distillation of the water, sodium bromide (0.019 lb per lb of starting compound) was added along with the oxidation solvent, glacial acetic acid (2.5 lb per lb of starting compound) and free radical initiator (0.075 lb of 30% aqueous hydrogen peroxide) per lb of starting compound. Oxidation using the recycled cobalt compound proceeded smoothly. The previously described oxidation reaction solution was heated to 90° C., agitated well, and sparged with air. The reaction was 70% complete in 4.5 hrs which is the expected rate under these conditions.

What is claimed is:

1. A process for recovering and recycling solvent in the oxidation of a 3-(substituted phenoxy) toluene feed to the corresponding 3-(substituted phenoxy) benzoic acid employing a combination of a cobalt compound and a bromide compound as catalyst which comprises:
   (a) distilling a first solvent from the oxidation reaction mixture containing 3-(substituted phenoxy)benzoic acid and cobalt compound;
   (b) combining solvent-depleted reaction mixture from (a) with a second solvent which dissolves the 3-(substituted phenoxy)benzoic acid and is capable of forming an immiscible layer with an aqueous solution of lower aliphatic carboxylic acid;
   (c) combining solution of 3-(substituted phenoxy)benzoic acid from (b) with an aqueous solution of lower aliphatic carboxylic acid which dissolves the cobalt compound to extract the cobalt compound from the solution;
   (d) separating the solution layer of 3-(substituted phenoxy)benzoic acid from the aqueous solution layer of lower aliphatic carboxylic acid and dissolved cobalt compound;
   (e) separating the aqueous solution of lower aliphatic carboxylic acid from extracted cobalt compound resulting from steps (c) and (d); and
   (f) recycling the first solvent recovered from (a) to serve as solvent in the oxidation of an additional quantity of 3-(substituted phenoxy)toluene feed.

2. The process of claim 1 in which the solvent in step (a) is acetic acid.

3. The process of claim 1 in which the cobalt compound is cobaltous acetate tetrahydrate.

4. The process of claim 1 in which the bromide compound is sodium bromide.

5. The process of claim 1 in which the 3-(substituted phenoxy)toluene starting compound has the structure

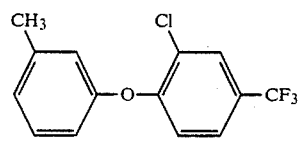

5-[2-chloro-4-(trifluoromethyl)phenoxy]toluene and the product compound has the structure

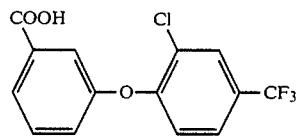

5-[2-chloro-4-(trifluoromethyl)phenoxy]benzoic acid.

6. The process of claim 2 in which distillation step (a) is effected in two cuts, the first cut removing water and the second cut removing aqueous acetic acid.

7. The process of claim 1 in which the solvent for 3-(substituted phenoxy)benzoic acid is methylene chloride.

8. The process of claim 1 in which the lower aliphatic carboxylic acid of step (c) is acetic acid.

9. The process of claim 1 in which acetic acid is the solvent used in step (a) and step (d) is carried out by flash distillation of said acetic acid.

10. The process of claim 5 in which step (d) is carried out by flash distillation of said acetic acid and 5-[2-chloro-4-(trifluoromethyl)phenoxy]toluene is employed as heat exchange medium in said flash distillation.

11. The process of claim 2 wherein the second solvent is methylene chloride and the aqueous solution of lower carboxylic acid from step (c) is an acetic acid solution.

12. The process of claim 11 wherein the methylene chloride/3-(substituted phenoxy)benzoic acid solution and the aqueous solution of lower aliphatic carboxylic/-dissolved cobalt compound solution form immiscible lower and upper layers, respectively to facilitate their separation in step (d).

13. A process for recovering and recycling solvent in the oxidation of a 3-(substituted phenoxy)toluene feed to the corresponding 3-(substituted phenoxy)benzoic acid employing a combination of a cobalt compound and a bromide compound as catalyst which comprises:
   (a) distilling a first solvent from the oxidation reaction mixture containing 3-(substituted phenoxy)benzoic acid and cobalt compound;
   (b) combining solvent-depleted reaction mixture from (a) with a second solvent which dissolves the 3-(substituted phenoxy)benzoic acid and is capable of forming an immiscible layer with an aqueous solution of lower aliphatic carboxylic acid;
   (c) combining solution of 3-(substituted phenoxy)benzoic acid from (b) with an aqueous solution of lower aliphatic carboxylic acid which dissolves the cobalt compound to extract the cobalt compound from the solution;
   (d) separating the solution layer of 3-(substituted phenoxy)benzoic acid from the aqueous solution layer of lower aliphatic carboxylic acid and dissolved cobalt compound; and
   (e) separating aqueous solution of lower aliphatic carboxylic acid from extracted cobalt compound resulting from step (c).

14. The process of claim 13 in which the solvent in step (a) is acetic acid.

15. The process of claim 13 in which the solvent for 3-(substituted phenoxy)benzoic acid is methylene chloride.

16. The process of claim 14 wherein the second solvent is methylene chloride and the aqueous solution of lower carboxylic acid from step (c) is an acetic acid solution.

17. The process of claim 16 wherein the methylene chloride 3-(substituted phenoxy)benzoic acid solution and the aqueous solution of lower aliphatic carboxylic-dissolved cobalt compound solution form immiscible lower and upper layers, respectively to facilitate their separation in step (d).

18. A process for recovering and recycling solvent in the oxidation of a 3-(substituted phenoxy)toluene feed to the corresponding 3-(substituted phenoxy)benzoic acid employing a combination of a cobalt compound and a bromide compound as catalyst which comprises:

(a) distilling an acetic acid solvent from the oxidation reaction mixture containing 3-(substituted phenoxy)benzoic acid and cobalt compound;

(b) combining solvent-depleted reaction mixture from (a) with methylene chloride solvent which dissolves the 3-(substituted phenoxy)benzoic acid;

(c) combining methylene chloride solution of 3-(substituted phenoxy)benzoic acid from (b) with an aqueous solution of acetic acid which dissolves the cobalt compound to extract the cobalt compound from the solution wherein the methylene chloride and acetic acid solutions form immiscible lower and upper layers respectively;

(d) separating the lower layer solution of 3-(substituted phenoxy)benzoic acid from the upper layer aqueous solution of lower aliphatic carboxylic acid and dissolved cobalt compound; and (e) separating the aqueous acetic acid solution from the extracted cobalt compound resulting from step (c).

19. The process of claim 18 wherein the cobalt compound is cobaltous acetate tetrahydrate and the bromide compound is sodium bromide.

* * * * *